(12) United States Patent
Sashida et al.

(10) Patent No.: US 7,563,913 B2
(45) Date of Patent: Jul. 21, 2009

(54) COMPOUND AND PHARMACEUTICAL COMPOSITION

(75) Inventors: Yutaka Sashida, Hachioji (JP); Yoshihiro Mimaki, Hachioji (JP); Minpei Kuroda, Nerima-ku (JP); Ryosuke Kobayashi, Hachioji (JP); Hiroaki Kando, Machida (JP); Kosuke Nosaka, Machida (JP); Hiroyasu Ishii, Tokyo (JP); Takao Yamori, Tokyo (JP)

(73) Assignee: Hiro International Co., Ltd., Tokyo-To (JP)

( * ) Notice: Subject to any disclaimer, the term of this patent is extended or adjusted under 35 U.S.C. 154(b) by 86 days.

(21) Appl. No.: 10/580,588

(22) PCT Filed: Nov. 25, 2003

(86) PCT No.: PCT/JP04/17480

§ 371 (c)(1),
(2), (4) Date: May 25, 2006

(87) PCT Pub. No.: WO2005/051955

PCT Pub. Date: Jun. 9, 2005

(65) Prior Publication Data

US 2007/0129427 A1 Jun. 7, 2007

(30) Foreign Application Priority Data

Nov. 27, 2003 (JP) ............................ 2003-397647
Sep. 13, 2004 (JP) ............................ 2004-265620

(51) Int. Cl.
*C07D 311/00* (2006.01)
*A61K 31/35* (2006.01)
(52) U.S. Cl. ...................................... 549/405; 514/454
(58) Field of Classification Search ................. 549/405; 514/545
See application file for complete search history.

(56) References Cited

FOREIGN PATENT DOCUMENTS

| JP | 02264722 | 10/1990 |
|---|---|---|
| JP | 07242559 | 9/1995 |
| JP | 08127538 | 5/1996 |

OTHER PUBLICATIONS

Pal et al. (Indian Journal of Chemistry, 14 (B), 259-252 (1976) and 15(B), 208-211, (1977).*
Pereira et al., Phytochemistry (1997), 45(7), 1445-1448, p. 1446.*
Gonzalez et al. Journal of Natural Products (1994), 57(3), 400-2.*
Baruah et al. Journal of Organic Chemistry, 1979, (44)11, 1831.*
Zdero et al. Phytochemistry (1987), 26(7), 1999-2006.*
Calis et al. Phytochemistry (2002), 59, 451-457.*

C. Zdero et al., "Germacranolides, Guaianolides and Eudesmanolides from Greenmaniella Resinosa", Phytochemistry, 1987, pp. 1999-2006, vol. 26, No. 7, pp. 1999-2006, 1987 Pergamon Journals Ltd.
W. Herz, "Structure of Tirotundin", Journal of Organic Chemistry, vol. 43, No. 6, 1978 pp. 1268-1270.
Raghwendra et al., "Chemical Constituents of Tithonia tagitiflora Desf.: Part III—Constitution of Tagitinin-A*", Indian Journal of Chemistry, Apr. 1976, pp. 259-262, vol. 14B.
Raghwendra et al., "Chemical Constituents of Tithonia tagitiflora Desf.*: Part IV—Tagitinins C, D & F", Indian Journal of Chemistry, Mar. 1977, pp. 208-211, vol. 15B.
Pereira et al., "Sesquiterpene Lactones from Brazilian Tithonia Diversifolia", Phytochemistry, 1997, pp. 1445-1448, vol. 45, No. 7.
Baruah et al., "Sesquiterpene Lactones of Tithonia deversifolia. Stereochemistry of the Tagitinins and Related Compounds", 1979, pp. 1831-1835, J. Org. Chem., vol. 44, No. 11.
Raghwendra et al., "Antileukemic and Other Constituents of Tithonia tagitiflora Desf.", Jun. 1976, pp. 918-920, vol. 65, No. 6.
Kobayashi et al., "Sequiterpenoids from the Aerial Parts of Tithonia deversifolia", Tokyo University of Pharmacy and Life Science, Hiro International Co., Ltd., Mar. 5, 2004.
Gonzalez et al., "4,5-Dihydroblumenol A, A New Nor-Isoprenoid from Perrottetia Multiflora", Mar. 1994, pp. 400-402, vol. 57, No. 3.
Shuster et al., "Sesquiterpene Lactones from Two Tithonia species", Phytochemistry, 1992, pp. 3139-3141, vol. 31, No. 9, 1992 Pergamon Press Ltd.
Zdero et al., "Germacranolides, Guaianolides and Eudesmanolides from Greenmaniella Resinosa", Phytochemistry, 1987, pp. 1999-2006, vol. 26, No. 7, 1987 Pergamon Journals Ltd.

(Continued)

*Primary Examiner*—D. Margaret Seaman
*Assistant Examiner*—Nizal S Chandrakumar
(74) *Attorney, Agent, or Firm*—The Webb Law Firm

(57) ABSTRACT

There are provided novel compounds that have been extracted and isolated from a plant belonging to the family Compositae. Compounds represented by general formula (I):

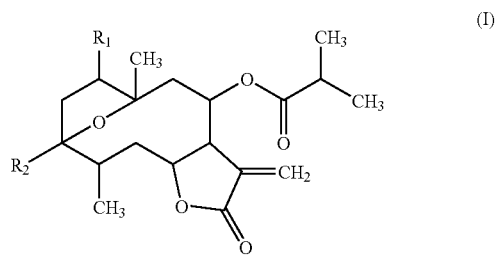

wherein $R_1$ represents hydroxyl and $R_2$ represents methoxy.

4 Claims, No Drawings

OTHER PUBLICATIONS

Shibata et al., "Studies on the Constituents of Japanese and Chinese Crude Drugs. III: Antispasmodic Action of Flavonoids and Anthraquinones", Faculty of Pharmaceutical Sciences, University of Tokyo and Pharmaceutical Faculty of Chiba University, Sep. 9, 1959, pp. 620-625, vol. 80.

Agata et al., "Studies on the Constituents of Medicinal Plants in Hokkaido. I: on the Whole Herb of Swertia tetrapetala Pall", Faculty of Pharmaceutical Sciences, Higashi Nippon Gakuen Unversity, Ishikari-Tobetsu, Hokkaido, 061-02, Japan, 1981, pp. 1067-1070, vol. 101, No. 11.

Macias et al., "Terpenoids with Potential Use as Natural Herbicide Templates", Biologically Active Natural Products: Agrochemicals, CRC Press LLC, 1999, pp. 15-31.

Jian-Qiao Gu et al., "Sesquiterpenoids from Tithonia diversifolia with Potent Cancer Chemopreventive Activity", J. Nat. Prod. 2002, vol. 65, No. 4, pp. 532-536.

Raghwendra Pal, et al., "Antileukemic and Other Constituents of Tithonia tagitiflora Desf.", Journal of Pharmaceutical Sciences, 1976, vol. 65, No. 6, pp. 918-920.

* cited by examiner

COMPOUND AND PHARMACEUTICAL COMPOSITION

BACKGROUND OF THE INVENTION

1. Field of the Invention

The present invention relates to novel compounds, particularly novel compounds, which have been extracted and isolated from plants belonging to the family Compositae or plants belonging to the genus *Ludwigia* of the family Onagraceae, and use of said novel compounds. Further, the present invention relates to use of known compounds, which have been extracted and isolated from plants belonging to the family Compositae or plants belonging to the genus *Ludwigia* of the family Onagraceae, in pharmaceutical preparations.

2. Description of Related Art

Plants belonging to the family Compositae or plants belonging to the genus *Ludwigia* of the family Onagraceae, particularly Tithonia diversifolia (Hemsl) A. Gray are known to have pharmacological effects, for example, inhibitory activity against skin diseases (tinea), hepatitis, icterus, and cystitis. For example, Japanese Patent No. 2609780 and Japanese Patent Application No. 127538/1996 propose antidiabetics using a decoction of Tithonia diversifolia (Hemsl) A. Gray or an extract thereof.

Further, compounds isolated from an extract of Tithonia diversifolia (Hemsl) A. Gray are disclosed in literature. For example, Raghwendra Pal, et al. Indian Journal of Chemistry, Section B: Organic Chemical Including Medicinal Chemistry, 14B, 259-262 (1976), Raghwendra Pal, et al. Indian Journal of Chemistry, Section B: Organic Chemical Including Medicinal Chemistry, 15B, 208-211 (1977), and Schuster A, et al. Phytochemistry, 31,3139-3141 (1992) disclose, in the order of the documents, compounds represented by general formula (I):

[Chemical formula 1]

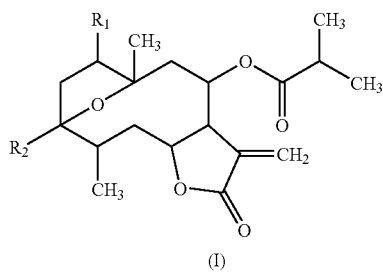

that is, a compound wherein $R_1$ and $R_2$ represent hydroxyl (hereinafter referred to as "TD-7"), a compound wherein $R_1$ represents a hydrogen atom and $R_2$ represents hydroxyl (hereinafter referred to as "TD-9"), and a compound wherein $R_1$ represents a hydrogen atom and $R_2$ represents methoxy (hereinafter referred to as "TD-10").

Paulo Sergio Pereira, et al. Phytochemistry, 45, 1445-1448 (1997), C. Zdero et al. Phytochemistry, 26, 1999-2006 (1987) discloses compounds represented by general formula (II):

[Chemical formula 2]

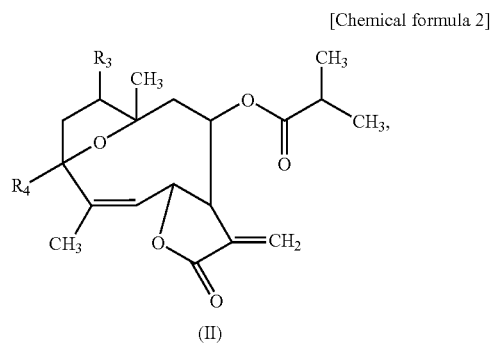

that is, a compound wherein $R_3$ and $R_4$ represent methoxy (hereinafter referred to as "TD-1") and a compound wherein $R_3$ represents methoxy and $R_4$ represents hydroxyl (hereinafter referred to as "TD-4").

Baruah Nabin C., et al. Journal of Organic Chemistry, 44, 1831-1835 (1979) discloses a compound represented by general formula (IV):

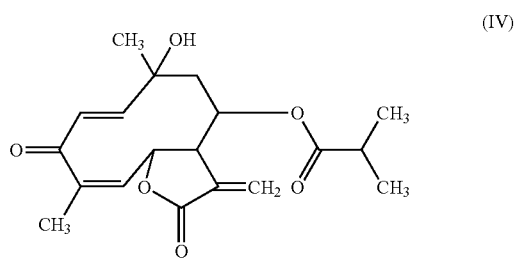

(hereinafter referred to as "TD-2").

Baruah Nabin C., et al. Journal of Organic Chemistry, 44, 1831-1835 (1979) discloses a compound represented by general formula (V):

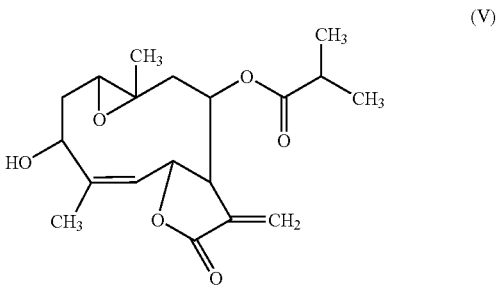

(hereinafter referred to as "TD-8").

Antonia G. Gonzalez, et al, Journal of Natural Products, 57, 400-402 (1994) discloses(4S,5R)-4-hydroxy-4-[(1E,3R)-3-hydroxy-1-butenyl]-3,3,5-trimethyl1-cyclo-hexanone).

On the other hand, Raghwendra Pal., et al. Journal of Pharmaceutical Science, 65, 918-920 (1976) reports that Tagitinin A to F have been isolated from an extract of Tithonia diversifolia (Hemsl) A. Gray and that, among these compounds, only Tagitinin F had the effect of prolonging the life span of mice in which P388 mouse leukemia was intraperitoneally transplanted. Here Tagitinin A corresponds to TD-7, Tagitinin C corresponds to TD-2, Tagitinin D corresponds to TD-9, and Tagitinin E corresponds to TD-8. However, Tagitinin F does not correspond to TD-1 to 10 according to the invention of this application.

Raghwendra Pal, et al. Indian Journal of Chemistry, Section B: Organic Chemistry Including Medicinal Chemistry, 15B, 208-211 (1977) discloses a compound represented by general formula (VI):

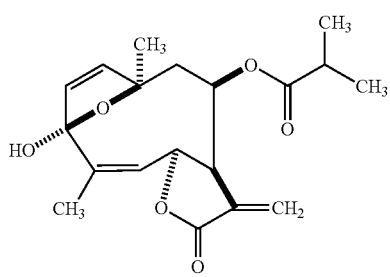

(VI)

(hereinafter referred to as "TD-11").

Isao Agata, et al. Yakugaku Zasshi, 101, 1067-1071 (1981) discloses a compound represented by general formula (VII):

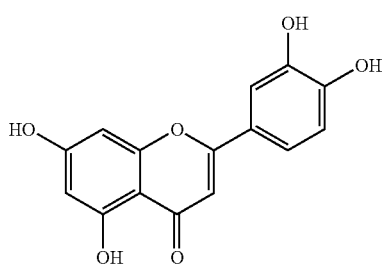

(VII)

(hereinafter referred to as "TD-12").

S. Shibata, et al. Yakugaku Zasshi, 80, 620-624 (1960) discloses a compound represented by general formula (VIII):

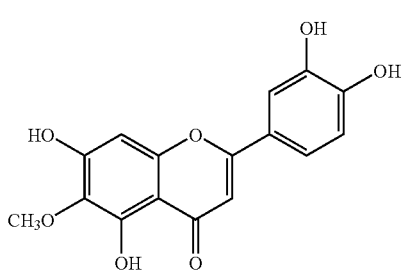

(VIII)

(hereinafter referred to as "TD-13").

Christa Zdero, et al. Phytochemistry, 26, 1999-2006 (1987) discloses a compound represented by general formula (IX):

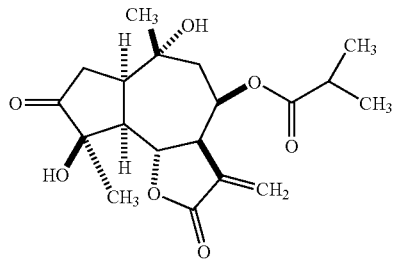

(IX)

(hereinafter referred to as "TD-14").

Unknown compounds, however, are present in plants belonging to the family Compositae or plants belonging to the genus *Ludwigia* of the family Onagraceae, and identification of these unknown compounds has been desired earnestly. Further, the development of new applications (such as pharmacological effect) of known and unknown compounds, which have been extracted and isolated from these plants, has also be urgently desired.

[Documents]

Patent document 1: Japanese Patent No. 2609780

Patent document 2: Japanese Patent Application No. 127538/1996

Technical Document 1: Raghwendra Pal, et al. Indian Journal of Chemistry, Section B: Organic Chemical Including Medicinal Chemistry, 14B, 259-262 (1976).

Technical Document 2: Raghwendra Pal, et al. Indian Journal of Chemistry, Section B: Organic Chemical Including Medicinal Chemistry, 15B, 208-211 (1977).

Technical Document 3: Schuster A, et al. Phytochemistry, 31, 3139-3141 (1992).

Technical Document 4: Paulo Sergio Pereira, et al. Phytochemistry, 45, 1445-1448 (1997).

Technical Document 5: C. Zdero et al. Phytochemistry, 26, 1999-2006 (1987).

Technical Document 6: Raghwendra Pal, et al. Indian Journal of Chemistry, Section B: Organic Chemical Including Medicinal Chemistry, 15B, 208-211 (1977).

Technical Document 7: Baruah Nabin C, et al. Journal of Organic Chemistry, 44, 1831-1835 (1979).

Technical Document 8: Antonia G. Gonzalez, et al, Journal of Natural Products, 57, 400-402 (1994)

Technical Document 9: Raghwendra Pal, et al. Journal of Phamaceutical Science, 65, 918-920 (1976).

Technical Document 10: Raghwendra Pal, et al. Indian Journal of Chemistry, Section B: Organic Chemistry Including Medicinal Chemistry, 15B, 208-211 (1977)

Technical Document 11: Isao Agata, et al. Yakugaku zasshi, 101, 1067-1071 (1981)

Technical Document 12: S. Shibata, et al. Yakugaku Zasshi, 80, 620-624 (1960)

Technical Document 13: Christa Zdero, et al. Phytochemistry, 26, 1999-2006 (1987)

SUMMARY OF THE INVENTION

The present inventors have now found novel compounds having anticancer activity and that certain known compounds have anticancer activity against specific cancer cells. The present invention has been made based on such finding. Accordingly, an object of the present invention is to provide novel compounds and use of known compounds having anti-cancer activity against specific cancer in pharmaceutical preparations.

First Aspect of Invention

According to a first aspect of the present invention, there are provided novel compounds represented by the following general formulae:

a compound represented by general formula (I):

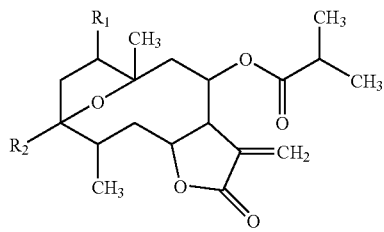

(I)

wherein $R_1$ represents hydroxyl and $R_2$ represents methoxy (hereinafter referred to as "TD-3");

a compound represented by general formula (II):

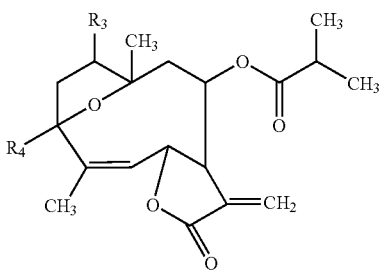

(II)

wherein $R_3$ represented hydroxyl and $R_4$ represents methoxy (hereinafter referred to as "TD-6"); and a compound represented by general formula (III):

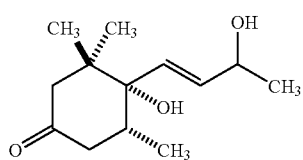

(III)

wherein 3-hydroxyl in 3-hydroxy-1-butenyl is in a 3S configuration (hereinafter referred to as "TD-5").

Second Aspect of Invention

According to a second aspect of the present invention, there are provided anti-acute myelogenous leukemia agents comprising one or at least two known compounds represented by the following general formulae:

a compound represented by general formula (I) wherein $R_1$ and $R_2$ represent hydroxyl (TD-7), a compound represented by general formula (I) wherein $R_1$ represents a hydrogen atom and $R_2$ represents hydroxyl (TD-9), a compound represented by general formula (I) wherein $R_1$ represents a hydrogen atom and $R_2$ represents methoxy (TD-10), a compound represented by general formula (II) wherein $R_3$ and $R_4$ represent methoxy (TD-1), a compound represented by general formula (II) wherein $R_3$ represents methoxy and $R_4$ represents hydroxyl (TD-4), a compound represented by general formula (IV):

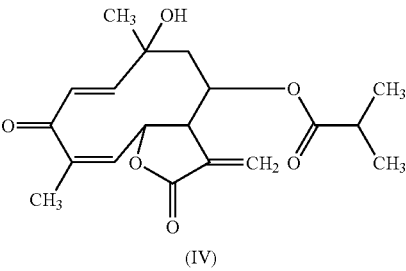

(IV)

(TD-2), and a compound represented by general formula (V):

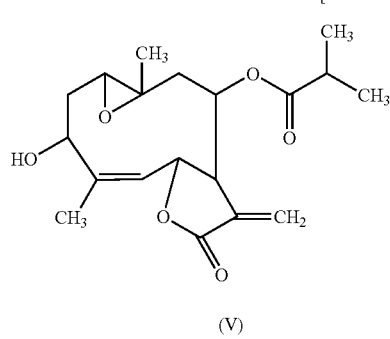

(V)

(TD-8).

Third Aspect of Invention

According to a third aspect of the present invention, there is provided an anti-ovarian cancer agent or an anti-prostatic cancer agent comprising as an active ingredient a compound represented by general formula (II) wherein $R_3$ and $R_4$ represent methoxy (TD-1). The present invention provides an anti-ovarian cancer agent or an anti-prostatic cancer agent for use in the treatment of an ovarian cancer or a prostatic cancer.

Fourth Aspect of Invention

According to a fourth aspect of the present invention, there is provided a method for isolating TD-1 to TD-14.

DETAILED DESCRIPTION OF THE PREFERRED EMBODIMENTS

First Aspect of Invention

The novel compounds provided in the first aspect of the present invention are a compound represented by general formula (I) wherein $R_1$ represents hydroxyl and $R_2$ represents methoxy (TD-3), a compound represented by general formula (II) wherein $R_3$ represents hydroxyl and $R_4$ represents methoxy (TD-6), and a compound represented by general formula (III) (TD-5).

TD-5 is an isomeric compound which is different from the compound described in technical document 8 in stereochemistry. Specifically, TD-5 is a novel compound in which hydroxyl in 3-hydroxy-1-butenyl is in a 3S configuration.

Use of Novel Compounds

Novel compounds TD-3, TD-5, and TD-6 according to the present invention are considered effective for use as an active ingredient for imparting, for example, an improvement in immunizing power, activation of metabolism function, subtractive and antimicrobial activities against pathogenic bacteria, effect of inhibiting excessive inflammation or allergy, and prevention and treatment of lifestyle-related diseases (for example, diabetes), and immunological diseases. Among these novel compounds, "TD-3" and "TD-6" have cytostatic activity and preferably have cytostatic (anticancer) activity against leukemia (more preferably acute myelogenous leukemia). Accordingly, "TD-3" and "TD-6" which are novel compounds can be used as an active ingredient of a cytostatic agent, and the cytostatic agent can be used for the treatment of cancers.

When "TD-3" and "TD-6" which are novel compounds are used as an anticancer agent for the treatment of cancers, these novel compounds may be formulated into various dosage forms by combining the compounds with conventional carriers for pharmaceuticals depending upon dosage forms. Examples of dosage forms include parenteral preparations, for example, those for subcutaneous injection, intravenous injection, and intramuscular injection and suppositories; preparations for systemic administration by oral administration, such as tablets, capsules, powders, and granules; and preparations for topical administration, such as ointments, lotions, suppositories, and aerosols.

The dose may be appropriately determined in consideration of the age, weight, and severity of condition of animals and humans.

Second Aspect of Invention

According to the second aspect of the present invention, there is provided an anti-acute myeloid leukemia agent comprising one or at least two known compounds. As described above, "TD-1", "TD-2", "TD-4", "TD-7", "TD-8", "TD-9", and "TD-10" are known compounds. The results of experiments conducted by the present inventors have shown that these known compounds have excellent inhibitory and therapeutic effects against acute myeloid leukemia of animals or humans (preferably). Accordingly, these TD compounds can be utilized as an active ingredient in anti-acute myeloid leukemia agents. Agents and dosage forms and the like as pharmaceuticals may be the same as those described above in connection with the first aspect of the present invention.

Third Aspect of Invention

According to the third aspect of the present invention, there is provided an anti-ovarian cancer agent or an anti-prostatic cancer agent comprising as an active ingredient a known compound "TD-1." The results of additional experiments have shown that TD-1 has excellent inhibitory and therapeutic effects against ovarian cancers or prostatic cancers of animals or humans (preferably). Accordingly, TD-1 can be utilized as an active ingredient in anti-ovarian cancer agents or anti-prostatic cancer agents. Agents and dosage forms and the like as pharmaceuticals may be the same as those described above in connection with the first aspect of the present invention.

Fourth Aspect of Invention

1) Production Process of Composition Comprising TD-1 to 10 (Extraction Method)

According to the present invention, there is provided a process for producing a composition comprising TD-1 to 10. This process comprises:

providing a raw material comprising TD-1 to 10;

extracting said raw material with a solvent optionally under heating; and supplying said extract to an ion-exchange chromatograph where said extract is subjected to solvent extraction with a first lower alcohol, a second lower alcohol, and optionally a lower ester in that order, whereby a composition comprising TD-1 to 10 is provided in a fraction of said second lower alcohol.

Raw Material

The raw material may be any one so far as TD-1 to 10 (and TD-11 to 14) are contained in a significant amount. Preferably, however, plants belonging to the family Compositae or plants belonging to the genus *Ludwigia* of the family Onagraceae may be mentioned as the raw material.

Specific examples of preferred plants belonging to the family Compositae include about 10 kinds of plants such as "Tithonia diversifolia (Hemsl) A, Gray," and cognate plants thereof such as "Tithonia fruticosa Canby & Rose," "Tithonia scaberrima Benth," and "Tithonia longeradiata (Bertol) Blake," and Mexican sunflower [scientific name: "Tithonia rotundifolia (Mill) Blake."

Specific examples of preferred plants belonging to the genus *Ludwigia* of the family Onagraceae include *Ludwigia octovalvis* Raven" and "*Ludwigia prostrata* Roxb."

Extraction Method

Specific examples of solvents usable in the extraction of the raw material comprising TD-1 to 10 include lower alcohols having 1 to 5 carbon atoms, preferably ethanol.

The first lower alcohol and the second lower alcohol may be the same or different. Preferably, however, the first lower alcohol and the second lower alcohol are different from each other. Alcohols having 1 to 6 carbon atoms, preferably 1 to 3 carbon atoms, may be mentioned as the first and second lower alcohols. In the present invention, a combination of methanol as the first lower alcohol with ethanol as the second lower alcohol is preferred. In a preferred embodiment of the present invention, from the viewpoint of realizing quick extraction in the ion exchange chromatography, preferably, the second lower alcohol is first introduced into the column followed by the use of a lower ester as the extraction solvent. The solvent extraction may be carried out with heating. The heating temperature is −20° C. or above and 100° C. or below. Preferably, the upper limit of the heating temperature is 80° C., and the lower limit of the heating temperature is 1° C.

The ion exchange chromatograph used may comprise a column packed with an ion exchange material (preferably a porous ion exchange resin: for example, "DIAION HP-20" manufactured by Mitsubishi Chemical Corporation.

After the solvent extraction, preferably, the solvent is evaporated for concentration to give an extract as a composition comprising compounds TD-1 to 10.

1-1) Isolation of TD-1 to 10

According to the present invention, there is provided a process for isolating compounds TD-1 to 10. This process comprises: providing a composition comprising TD-1 to 10; and repeating the separation of said composition by chromatography a plurality of times to obtain compounds TD-1 to 10.

In a preferred embodiment of the present invention, the composition produced by the above production process is utilized as the composition comprising TD-1 to 10. Separation solvents usable herein include water, acetone, chloroform, lower alcohols having 5 or less carbon atoms, lower esters having 5 or less carbon atoms, and mixed solvents composed of these solvents. The chromatography used may be of either normal phase type or reverse phase type. The filler may be a porous material (preferably silica gel). (High performance) Liquid chromatography may also be used. In the present invention, preferably, TD compounds are isolated by a combination of these chromatographic techniques.

Specific examples of methods usable for isolating compounds TD-1 to 10 according to the present invention are as follows. The column packing material, chromatograph, extraction solvent and the like may be the same as those described above in connection with the process for isolating TD compounds.

1-2) Fractionation of Compositions Comprising TD-1 to 10

According to the present invention, there is provided a process for separating, from a composition comprising TD-1 to 10, a first composition comprising TD-1 to 8 and a second composition comprising TD-9 and 10. In this process, the composition comprising TD-1 to 10 is separated by normal phase column chromatography and then by reverse phase column chromatography into two compositions, a first composition comprising TD-1 to 8 and a second composition comprising TD-9 and 10.

According to the present invention, there is provided a process for isolating TD-1 to 10 from the first composition comprising TD-1 to 8 and the second composition comprising TD-9 and 10. This process will be described in more detail.

1-3) Isolation of TD-1, 2, 4 and 5

TD-1, TD-2, TD-4, and TD-5 each can be isolated by repeatedly subjecting the first composition comprising TD-1 to 8 to normal phase or reverse phase (silica gel) column chromatography and further conducting (high performance) liquid chromatography.

In a more preferred embodiment of the present invention, TD-1, TD-2, TD-4, and TD-5 each can be isolated by subjecting the first composition comprising TD-1 to 8 to separation and purification by reverse phase column chromatography on silica gel, reverse phase column chromatography on silica gel, and high performance liquid chromatography equipped with a reverse phase silica gel column in that order.

1-4) Isolation of TD-3 and 7

TD-3 and TD-7 each can be isolated by repeatedly subjecting the first composition comprising TD-1 to 8 to normal phase or reverse phase column chromatography on silica gel.

In a more preferred embodiment of the present invention, TD-3 and TD-7 each can be isolated by subjecting the first composition comprising TD-1 to 8 to separation and purification by normal phase column chromatography on silica gel, reverse phase column chromatography on silica gel, and reverse phase column chromatography on silica gel in that order.

1-5) Isolation of TD-6 and 8

TD-6 and TD-8 each can be isolated by repeatedly subjecting the first composition comprising TD-1 to 8 to normal phase or reverse phase column chromatography on silica gel.

In a more preferred embodiment of the present invention, TD-6 and TD-8 each can be isolated by subjecting the first composition comprising TD-1 to 8 to separation and purification by normal phase column chromatography on silica gel, reverse phase column chromatography on silica gel, and reverse phase column chromatography on silica gel in that order.

1-6) Isolation of TD-9 and 10

TD-9 and TD-10 each can be isolated by repeatedly subjecting the second composition comprising TD-9 and 10 to normal phase or reverse phase column chromatography on silica gel.

In a more preferred embodiment of the present invention, TD-9 and 10 each can be isolated by subjecting the second composition comprising TD-9 and 10 to purification by normal phase column chromatography on silica gel, normal phase column chromatography on silica gel, and reverse phase column chromatography on silica gel in that order.

2) Production Process of Composition Comprising TD-11 to 14 (Extraction)

The production process of a composition comprising TD-11 to 14 may be the same as described above in the item 1) Production process of composition comprising TD-1 to 10 (extraction method). Accordingly, the raw material and extraction method described in the item 1) as such may be applied to the production process of the composition comprising TD-11 to 14. In the production process, TD-11 to 14 may be obtained as a composition comprising a mixture of TD-11 to 14 with TD-1 to 10.

2-1) Isolation of TD-11 to 14

According to the present invention, there is provided a process for isolating compounds TD-11 to 14. This process comprises: providing a composition comprising TD-11 to 14; and repeating the separation of said composition by chromatography a plurality of times to obtain compounds TD-11 to 14.

In the present invention, the isolation of TD-11 to 14 may be carried out in the same manner as in the isolation of TD-1 to 10. In this isolation, TD-11 to 14 may be obtained as a composition comprising a mixture of TD-11 to 14 with TD-1 to 10.

2-2) Fractionation of Compositions Comprising TD-11 to 14

According to the present invention, there is provided a process for separating, from a composition comprising TD-11 to 14, a third composition comprising TD-11 and TD-14 and a fourth composition comprising TD-12 and TD-13. In this process, the composition comprising TD-11 to 14 is separated by normal phase column chromatography and then by reverse phase column chromatography into a third composition comprising TD-11 and TD-14 and a fourth composition comprising TD-12 and TD-13.

In a preferred embodiment of the present invention, there is provided a process for producing first to fourth compositions using a composition comprising TD-1 to TD-14. This process may be carried out in the same manner as in the above item 1-2) Fractionation of compositions comprising TD-1 to 10 and the above item 2-2) Fractionation of compositions comprising TD-11 to 14. Specifically, in this process, the composition comprising TD-1 to TD-14 is separated by normal phase column chromatography and then by reverse phase column chromatography into a first composition comprising TD-1 to 8, a second composition comprising TD-9 and 10, a third composition comprising TD-11 and TD-14, and a fourth composition comprising TD-12 and TD-13. In a preferred embodiment of the present invention, TD-1 to TD-14 each can be isolated from the first to fourth compositions by the above processes or processes which will be described later.

2-3) Isolation of TD-11 and 14

TD-11 and 14 each can be isolated by repeatedly subjecting the third composition comprising TD-11 and 14 to normal phase or reverse phase column chromatography on silica gel. In a more preferred embodiment of the present invention, TD-11 and 14 each can be isolated by subjecting the third composition comprising TD-11 and 14 to separation and purification by normal phase column chromatography on silica gel, reverse phase column chromatography on silica gel, and reverse phase column chromatography on silica gel in that order.

2-4) Isolation of TD-12 and 13

TD-12 and 13 each can be isolated by repeatedly subjecting the fourth composition comprising TD-12 and 13 to normal phase or reverse phase column chromatography on silica gel. In a more preferred embodiment of the present invention, TD-12 and 13 each can be isolated by subjecting the fourth composition comprising TD-12 and 13 to purification by normal phase column chromatography on silica gel, reverse phase column chromatography on silica gel, and reverse phase column chromatography on silica gel in that order.

EXAMPLES

Extraction and Fractionation of Compounds TD-1 to 14

The aerial parts of Tithonia diversifolia (Hemsl) A. Gray (Dried Powder (3.0 kg) ) was heat extracted with 45 liters of 80% ethanol at 65° C. for 2 hr. The extract was then filtered to remove impurities, and the solvent was then removed to give a concentrated extract.

This concentrated extract (320 g) was filled into an ion-exchanged column chromatograph (ion exchanger: Diaion HP-20). Next, a first alcohol solvent (methanol:water ratio=50% or more) was allowed to flow into the column. Next, 45 liters of a second alcohol solvent (80% ethanol) was allowed to flow into the column. Finally, ethyl acetate as a lower ester was allowed to flow into the column, and heat extraction was carried out at 65° C. for 2 hr to give a second alcohol fraction. This second alcohol fraction was filtered to remove impurities, and the second alcohol solvent was then evaporated to give a concentrated extract.

Next, this extract (320 g) was subjected to normal phase column chromatography on silica gel (solvent: 9:1 mixture of chloroform and methanol) and reverse phase column chromatography on silica gel (packing material: ODS silica gel, solvent: 1:1 mixture of methanol and water) to give fraction 2-1 (containing TD-1 to 8), fraction 2-2 (containing TD-11 and 14), fraction 2-3 (containing TD-9 and 10), and fraction 2-4 (containing TD-12 and 13). In the normal phase column chromatography on silica gel, a difference in adsorbability onto the silica gel as a fixed phase was utilized, and, in the reverse phase column chromatography on ODS silica gel, silica gel with the surface being substituted by octadecyl groups was used as the packing material to utilize distribution between the fixed phase (ODS silica gel) and the mobile phase (solvent), whereby the above four fractions were separated.

Each of fractions 2-1 to 2-4 was subjected to the following treatment to isolate each TD compound.

Fraction 2-1/Isolation of TD-1, 2, 4 and 5

A part of fraction 2-1 was successively purified by normal phase column chromatography on silica gel (solvent: 9:1 mixture of chloroform and acetone and 49:1 mixture of chloroform and acetone), reverse phase column chromatography on silica gel (solvent: 2:3 mixture of acetonitrile and water), reverse phase column chromatography on silica gel (solvent: 11:9 mixture of methanol and water), and high performance liquid chromatography (HPLC) using a reverse silica gel column (solvent: 7:3 mixture of methanol and water and 3:2 mixture of methanol and water) to isolate TD-1 (28.0 mg), TD-2 (14.0 mg), TD-4 (35.3 mg), and TD-5 (13.0 mg).

Fraction 2-1/Isolation of TD-3 and 7

A part of fraction 2-1 was successively purified by normal phase column chromatography on silica gel (solvent: 49:1 mixture of chloroform and acetone), reverse phase column chromatography on silica gel (solvent: 11:9 mixture of methanol and water), and reverse phase column chromatography on silica gel (solvent: 1:2 mixture of acetonitrile and water) to isolate TD-3 (56.2 mg) and TD-7 (50.0 mg).

Fraction 2-1/Isolation of TD-6 And 8

A part of fraction 2-1 was successively purified by normal phase column chromatography on silica gel (solvent: 49:1 mixture of chloroform and acetone and 19:1 mixture of chloroform and acetone), reverse phase column chromatography on silica gel (solvent: 3:2 mixture of methanol and water), and reverse phase column chromatography on silica gel (solvent: 1:2 mixture of acetonitrile and water) to isolate TD-6 (14.0 mg) and TD-8 (8.7 mg).

Fraction 2-3/Isolation of TD-9 and 10

Fraction 2-3 was successively purified by normal phase column chromatography on silica gel (solvent: 19:1 mixture of chloroform and acetone, 4:1 mixture of chloroform and acetone, and 2:1 mixture of chloroform and acetone), normal phase column chromatography on silica gel (solvent: 9:1 mixture of hexane and acetone and 7:3 mixture of hexane and acetone), and reverse phase column chromatography on silica gel (solvent:

9:1 mixture of acetonitrile and water, 4:1 mixture of acetonitrile and water, 3:1 mixture of acetonitrile and water, 2:1 mixture of acetonitrile and water, and 1:1 mixture of acetonitrile and water) to isolate TD-9 (8.4 mg) and TD-10 (7.8 mg).

Fraction 2-2/Isolation of TD-11 and 14

Fraction 2-2 was successively purified by normal phase column chromatography on silica gel (solvent: 49:1 mixture of chloroform and acetone), reverse phase column chromatography on silica gel (solvent: 1:1 mixture of methanol and water), and reverse phase column chromatography on silica gel (solvent: 3:1 mixture of acetonitrile and water, 5:8 mixture of acetonitrile and water, and 1:2 mixture of acetonitrile and water) to isolate TD-11 (67.9 mg) and TD-14 (8.7 mg).

Fraction 2-4/Isolation of TD-12 and 13

Fraction 2-4 was successively purified by normal phase column chromatography on silica gel (solvent: 4:1 mixture of chloroform and acetone and 3:2 mixture of chloroform and acetone), reverse phase column chromatography on silica gel (solvent: 1:1 mixture of methanol and water), and reverse phase column chromatography on silica gel (solvent: 1:2 mixture of acetonitrile and water, 1:1 mixture of acetonitrile and water, and 2:1 mixture of acetonitrile and water) to isolate TD-12 (18.8 mg) and TD-13 (60.8 mg).

Determination of Structures of TD-1 to 14

The structures of TD-1 to TD-14 prepared above were determined.

(1) Determination of Structures of Novel Compounds

For novel compounds, TD-3, TD-5 and TD-6, the structure was determined based on the following spectral data and the like.

TD-3 ($C_{20}H_{30}O_7$)
(1S,3R,4S,6R,7S,8R,10R)-1-hydroxy-3-methoxy-3,10-epoxy-8-isobutyryloxygermacra-11(13)-en-6,12-olide 1) Properties: White powder $[\alpha]_D^{26}$-102 (methanol) 2) HR-ESI-MS m/z: 383.2058 (Calcd. for $C_{20}H_{31}O_7$; 383.2070). 3) UV (methanol) $\lambda_{max}$ (log ε): 216 (log ε=3.81) 4) IR (film) cm$^{-1}$: 3446, 2972, 2933, 1761, 1736, 1460, 1317, 1261, 1194, 1155, 1072, 1007, 984. 5) $^1$H-NMR (deutrochloroform) ppm: 6.19 (1H, d, J=3.4 Hz, H-13a), 5.54 (1H, ddd, J=11.4, 5.3, 2.6 Hz, H-8), 5.47 (1H, d, J=2.9 Hz, H-13b), 4.46 (1H, ddd, J=10.6, 6.9, 1.1 Hz, H-6), 4.06 (1H, dd, J=9.5, 8.6 Hz, H-1), 3.92 (1H, m, H-7), 3.10 (3H, s, OMe), 2.49 (1H, dd, J=14.5, 9.5 Hz, H-2b), 2.37 (1H, m, H-2'), 2.06 (1H, m, H-5b), 1.99 (1H, m, H-4), 1.97 (1H, dd, J=14.5, 5.4 Hz, H-9a), 1.81 (1H, dd, J=14.5, 8.6 Hz, H-2a), 1.72 (1H, br d, J=13.3 Hz, H-5a), 1.63 (1H, dd, J=14.5, 11.4 Hz, H-9b), 1.37 (3H, s, Me-14), 1.01 and 0.99 (each 3H, d, J=7.0 Hz, Me-3' and Me-4'), 0.99 (3H, d, J=7.0 Hz, Me-15). 6) $^{13}$C-NMR (deutro-chloroform) ppm: 79.7 (C-1), 41.7 (C-2), 108.8 (C-3), 46.4 (C-4), 38.2 (C-5), 82.3 (C-6), 48.2 (C-7), 70.2 (C-8), 35.1 (C-9), 81.3 (C-10), 137.7 (C-11), 169.8 (C-12), 121.7 (C-13), 24.1 (C-14), 18.3 (C-15), 176.7 (C-1'), 34.5 (C-2'), 19.1 (C-3' or C-4'), 19.6 (C-3'and C-4'), 49.2 (OMe).

TD-5 ($C_{13}H_{22}O_3$)
(4S, 5R)-4-hydroxy-4-[(1E, 3S)-3-hydroxy-1-butenyl]-3,3,5-trimethyl-cyclohexanone)

1) Properties: White powder $[\alpha]_D^{26}$-8 (methanol) 2) HR-ESI-MS m/z: 227.1050 (Calcd. for $C_{13}H_{22}O_3$; 227.1647). 3) IR (film) cm$^{-1}$: 3415, 2968, 11900, 2877, 1695, 1454, 1412, 1369, 1286, 1140, 1061, 1030, 977, 939. 4) $^1$H-NMR (deutro-chloroform) ppm: 2.77 (1H, d, J=13.6 Hz, H-2ax), 1.84 (1H, dd, J=13.6, 2.2 Hz, H-2ax), 2.35 (1H, t-like, J=12.9 Hz, H-4ax), 2.13 (1H, ddd, J=13.6, 4.5, 2.2 Hz, H-4eq), 2.19 (1H, ddq, J=12.9, 6.5, 4.5 Hz, H-5), 5.63 (1H, dd, J=15.8, 0.8 Hz, H-7), 5.77 (1H, dd, J=15.8, 5.7 Hz, H-8), 4.36 (1H, ddd, J=6.4, 5.7, 0.8 Hz, H-9), 1.25 (3H, d, J=6.4 Hz, Me-10), 0.87 (3H, s, Me-11), 0.90 (3H, s, Me-12), 0.81 (3H, d, J=6.5 Hz, Me-13). 5) $^{13}$C-NMR (deutro-chloroform) ppm: 42.5 (C-1), 51.4 (C-2), 211.4 (C-3), 45.1 (C-4), 36.4 (C-5), 77.0 (C-6), 131.8 (C-7), 135.2 (C-8), 68.3 (C-9), 23.9 (C-10), 24.5 (C-11), 24.4 (C-12), 15.9 (C-13).

TD-6 ($C_{20}H_{28}O_7$)
(1S,3R,6R,7R,8R,10R)-1-hydroxy-3-methoxy-3,10-epoxy-8-isobutyryloxygermacra-4,11(13)-dien-6,12-olide 1) Properties: White powder $[\alpha]_D^{26}$-110(methanol) 2) HR-ESI-MS m/z: 381.1947 (Calcd. for $C_{20}H_{29}O_7$; 381.1913). 3) UV (methanol) $\lambda_{max}$ (log ε) 213 (log ε=3.88) 4) IR (film) cm$^{-1}$: 3421, 2972, 1763, 1732, 1587, 1282, 1186, 1111, 1064, 991 5) $^1$H-NMR (deutro-chloroform) ppm: 6.20 (1H, d, J=2.8 Hz, H-13a), 5.66 (1H, m, H-5), 5.59 (1H, ddd, J=11.2, 5.0, 4.6 Hz, H-8), 5.55 (1H, d, J=2.3 Hz, H-13b), 5.20 (1H, m, H-6), 4.16 (1H, m, H-7), 3.77 (1H, dd, J=11.1, 3.9 Hz, H-1), 3.11 (3H, s, OMe), 2.91 (1H, br d, J=11.3 Hz, H-2b), 2.34 (1H, m, H-2'), 2.31 (1H, m, H-2a), 1.82 (1H, dd, J=14.1, 5.0 Hz, H-9a), 1.70 (3H, t-like, J=1.8 Hz, Me-15), 1.66 (1H, dd, J=14.1, 11.2 Hz, H-9b), 1.44 (3H, s, Me-14), 1.00 (3H, d, J=7.1 Hz, Me-3' or Me-4'), 0.97 (3H, d, J=7.2 Hz, Me-3' or Me-4'). 6) $^{13}$C-NMR (deutro-chloroform) ppm: 77.1 (C-1), 45.2 (C-2), 109.7 (C-3), 138.4 (C-4), 131.2 (C-5), 75.8 (C-6), 49.6 (C-7), 71.2 (C-8), 39.7 (C-9), 87.5 (C-10), 136.2 (C-11), 169.5 (C-12), 122.7 (C-13), 20.8 (C-14), 21.6 (C-15), 175.9 (C-1'), 334.0 (C-2'), 18.6 (C-3' or C-4'), 19.0 (C-3' or C-4'), 50.1 (OMe).

(2) Determination of Structures of Known Compounds

A) TD-1, TD-2, TD-4, TD-7, TD-8, TD-9, and TD-10 are known compounds, and the structuers of these compounds were determined based on the contents of description in the above-described technical documents 1 to 13 using various spectral data. Specific results were as follows.

TD-1
(1R,3R,6R,7R,8R,10R)-1,3-dimethoxy-3,10-epoxy-8-isobutyryloxygermacra-4,11(13)-dien-6,12-olide TD-2
(6S,7R,8R,10R)-10-hydroxy-3-oxo-8-isobutyryloxygermacra-1,4,11(13)-trien-6,12-olide TD-4
(1R,3R,6R,7R,8R,10R)-3-hydroxy-1-methoxy-3,10-epoxy-8-isobutyryloxygermacra-4,11(13)-dien-6,12-olide TD-7
(1S,3R,4S,6R,7S,8R,10R)-1,3-dihydroxy-3,10-epoxy-8-isobutyryloxygermacra-11(13)-en-6,12-olide TD-8
(1R,3S,6S,7R,8R,10R)-3-hydroxy-1,10-epoxy-8-isobutyrylgermacra-4,11(13)-dien-6,12-olide TD-9
(3R,4S,6R,7S,8R,10S)-3-hydroxy-3,10-epoxy-8-isobutyryloxygermacra-11(13)-en-6,12-olide TD-10
(3R,4S,6R,7S,8R,10S)-3-methoxy-3,10-epoxy-8-isobutyryloxygermacra-11(13)-en-6,12-olide B) TD-11 to 14 are known compounds, and the structures of these compounds were determined based on the contents of description in the above-described technical documents 10 to 13 using various spectral data. Specific results were as follows.

TD-11 (Generic name: Tagitinin F)
(3R,6R,7R,8R,10R)-3-hydroxy-3,10-epoxy-8-isobutyryloxygermacra-1,4,11(13)-trien-6,12-olide TD-12 (Generic name: Luteolin)
3',4'5,7-tetrahydroxy-flavone TD-13 (Generic name: Nepetin)
3',4',5,7-tetrahydroxy-6-methoxy-flavone TD-14
7a, 10a-dihydroxy-3-oxo-8b-isobutyryloxyguaia-11(13)-en-12,6a-olide Evaluation Tests
Evaluation Test 1: Evaluation Test for TD-1 to 10

Cytostatic activity of TD-1 to 10 was studied in terms of numerical values of cytotoxic activity using human acute myeloid leukemia cell strain HL-60. The test was specifically carried out according to the following procedure.

HL-60 cells precultured in an FBS-containing RPMI 1640 medium were suspended in an FBS-containing RPMI 1640 medium so that the number of HL-60 cells is $4\times10^4$ per mL. The suspension was dispensed in an amount of 196 mL for each well in a 96-well microplate, followed by preincubation in 5% carbon dioxide gas at 37° C. for 24 hr. Subsequently, EtOH-$H_2O$(1:1) as control, and a solution of each TD compound in EtOH-$H_2O$(1:1) as a sample were added each in an amount of 4 mL to each well. After incubation in 5% carbon dioxide gas at 37° C. for 72 hr, an MTT reagent was added in an amount of 10 mL to each well, and incubation was further carried out for 4 hr. The medium was removed, and MTT formazan thus produced was then dissolved in 175 mL of DMSO. Detection was carried out at a light absorption wavelength of 550 nm with a microplate reader, and the viable cell count based on the control was calculated. $IC_{50}$ values were calculated from a dose-response curve.

The $IC_{50}$ values (μg/mL) of TD-1 to 10 were as summarized in Table 1 below.

TABLE 1

| Compound | $IC_{50}$ value, μg/mL |
|---|---|
| TD-1 | (0.60) |
| TD-2 | (0.38) |
| TD-3 | (4.97) |
| TD-4 | (0.05) |
| TD-6 | (2.50) |
| TD-7 | (3.87) |
| TD-8 | (0.92) |
| TD-9 | (2.50) |
| TD-10 | (0.78) |

Evaluation Test 2: Evaluation Test for TD-1 (Cytostatic Activity Test)

To examine the cytostatic activity of TD-1, a human cultured cancer cell panel screening test was carried out. Specifically, for TD-1, the human cultured cancer cell panel screening test was carried out by measuring 50% cell growth inhibitory concentration ($GI_{50}$) against 39 types in total of human tumor cells according to the method described in "Gan To Kagaku Ryoho (Cancer and Chemotherapy) (Takao Yamori), 24, 129-135, 1997". The results were as summarized in Table 2 below.

TABLE 2

| TD-1 | $GI_{50}$, μM |
|---|---|
| Average value for 39 types in total of cancer cells | 6.8 |
| Ovarian cancer cell line | |
| OVCAR-3 | 3.3 |
| OVCAR-4 | 5.6 |
| OVCAR-5 | 2.9 |
| OVCAR-8 | 3.6 |
| SK-OV-3 | 4.0 |
| Prostatic cancer cell line | |
| DU-145 | 4.2 |
| PC-3 | 3.3 |

Evaluation Results

As is apparent from the results shown in Table 2, for TD-1, the $GI_{50}$ values against the ovarian cancer cell lines and the prostatic cancer cell lines were lower than the average $GI_{50}$ value against 39 types in total of cancer cells, indicating that TD-1 has cytostatic activity against these cancer cell lines.

The invention claimed is:

1. A compound represented by general formula (I):

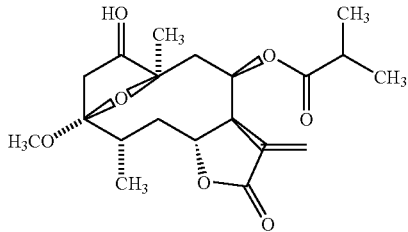

(1S,3R,4S,6R,7S,8R,10R)-1-hydroxy-3-methyloxy-3,10-epoxy-8-isobutyryloxygermacra-11(13)-en-6,12-olide.

2. A compound represented by general formula (II):

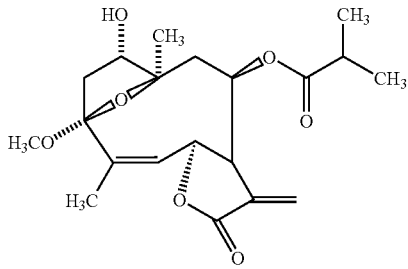

(1S,3R,6R,7R,8R,10R)-1-hydroxy-3-methoxy-3,10-epoxy-8-isobutyryloxygermacra-4,11(13)-dien-6,12-olide.

3. A compound represented by general formula (III):

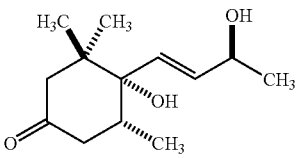

(4S,5R)-4-hydroxy-4-[(1E,3S)-3-hydroxy-1-buteneyl]-3,3,5-trimethyl cyclohexanone.

4. A compound represented by general formula (I):

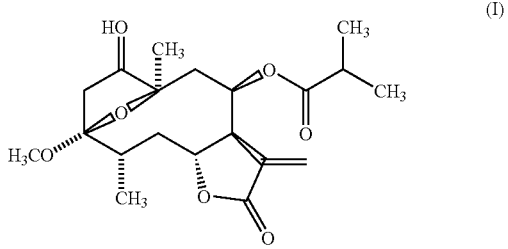

(1S,3R,4S,6R,7S,8R, 10R)-1-hydroxy-3-methyloxy-3,10-epoxy-8-isobutyryloxygermacra-11(13)-en-6,12-olide,
wherein said compound is produced by a process comprising:
(a) providing a composition comprising the compound of formula (I), a compound represented by general formula (II):

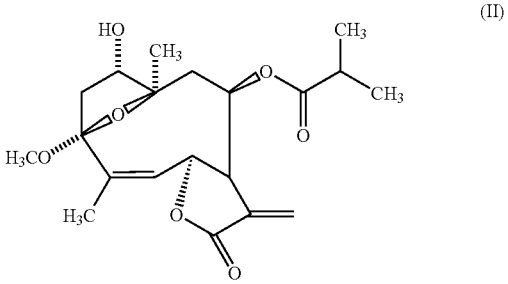

(1S,3R,6R,7R,8R,10R)-1-hydroxy-3-methoxy-3,10-epoxy-8-isobutyryloxygermacra-4,11(13)-dien-6,12-olide,
and a compound represented by general formula (III):

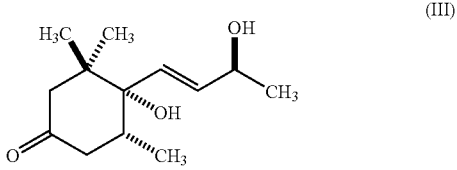

(4S,5R)-4-hydroxy-4-[(1E,3S)-3-hydroxy-1-buteneyl]-3,3,5-trimethyl cyclohexanone; and
(b) repeating separation of said composition by chromatography a plurality of times to obtain the compound of formula (I).

* * * * *

UNITED STATES PATENT AND TRADEMARK OFFICE
CERTIFICATE OF CORRECTION

PATENT NO.        : 7,563,913 B2                              Page 1 of 1
APPLICATION NO.   : 10/580588
DATED             : July 21, 2009
INVENTOR(S)       : Sashida et al.

It is certified that error appears in the above-identified patent and that said Letters Patent is hereby corrected as shown below:

Title Page, See Item (22) PCT Filed: "Nov. 25, 2003" should read
-- Nov. 25, 2004 --

Title Page, See Item (56) References Cited, OTHER PUBLICATIONS,
column 2, the 8th entry, "Kobayashi et al., "Sequiterpenoids...." should read
-- Kobayashi et al., "Se_s_quiterpenoids.... --

Signed and Sealed this

Twenty-sixth Day of January, 2010

David J. Kappos
*Director of the United States Patent and Trademark Office*